United States Patent
Saito et al.

(10) Patent No.: US 6,683,933 B2
(45) Date of Patent: Jan. 27, 2004

(54) THREE-DIMENSIONAL IMAGE DISPLAY DEVICE IN NETWORK

(75) Inventors: Motoaki Saito, San Mateo, CA (US); Vikram Simha, Lexington, MA (US); Kazuo Takahashi, San Mateo, CA (US); Tiecheng Zhao, Norwood, MA (US)

(73) Assignee: TeraRecon, Inc., San Mateo, CA (US)

(*) Notice: Subject to any disclaimer, the term of this patent is extended or adjusted under 35 U.S.C. 154(b) by 84 days.

(21) Appl. No.: 10/136,536

(22) Filed: May 1, 2002

(65) Prior Publication Data

US 2002/0186820 A1 Dec. 12, 2002

(30) Foreign Application Priority Data

May 2, 2001 (JP) .......................................... 2001-171766

(51) Int. Cl.⁷ ................................................. A61B 6/03
(52) U.S. Cl. ............................................. 378/4; 378/94
(58) Field of Search ............................ 378/4, 8, 15, 901

(56) References Cited

U.S. PATENT DOCUMENTS 5,986,662 A * 11/1999 Argiro et al. ............... 345/424
6,219,059 B1 * 4/2001 Argiro ........................ 345/424
2002/0118206 A1 * 8/2002 Knittel ........................ 345/557

* cited by examiner

Primary Examiner—David V. Bruce
(74) Attorney, Agent, or Firm—Blakely, Sokoloff, Taylor & Zafman LLP

(57) ABSTRACT

A three-dimensional image processing system enables multiple users at distant locations employing ordinary personal computers to construct and observe three-dimensional images simultaneously. In a network environment, a three-dimensional image processing device acquires image data and incorporates it into three-dimensional voxels based on instructions from the computers. The device operates on the three-dimensional voxels using object space domain, opacity and color parameters to construct three-dimensional data and operates on the three-dimensional data using projection processing parameters to construct three-dimensional images. The system sets projection processing parameters for constructing three-dimensional images from three-dimensional data and displays three-dimensional images which may be routed to the various computers via the network.

7 Claims, 11 Drawing Sheets

THREE-DIMENSIONAL IMAGE DISPLAY DEVICE IN NETWORK

The present invention relates to a three-dimensional image display device for displaying the spatial distribution of the physical matter of a specimen in the form of a three-dimensional image.

BACKGROUND OF THE INVENTION

Since the advent of the potential for producing precision tomogram data showing the physical matter of a body using x-ray CT devices, it has become possible to render three-dimensional images using multiple sets of tomogram data captured from different cross-section positions. In particular, it has become possible to reconstitute three-dimensional images with even greater precision due to the recent use of helical scan x-ray CT devices and multi-beam x-ray CT devices.

In order to construct a precise three-dimensional image, it is desirable to make the cross-section images and cross-section image spacing as narrow as possible in terms of the cross-sections that are used in constructing the three-dimensional image. With recently implemented multi-beam x-ray CT devices, x-ray detectors are divided along the body axis of the specimen perpendicular to the cross-sections, and by this means, more narrow cross-section image spacing (slice gap) and thinner cross-section images (slice width) have been achieved relative to conventional x-ray CT devices.

When using image data having narrow cross section gaps and cross section thicknesses captured using multi-beam x-ray CT devices, it is possible to produce three-dimensional images that are more detailed than those obtained using image data captured with a conventional x-ray CT device. For this reason, the range of diagnostic use of three-dimensional images produced using x-ray CT image data is greatly increased, and the technology is being used towards a wider variety of ends.

With multi-beam x-ray CT devices, it is possible to capture image data with thin cross-sections and narrow cross-section image gaps more rapidly than with conventional x-ray CT devices. However, the clinical requirement in terms of length along the axis of a body is the same as in the past, so the number of image data slices or image data volume is greatly increased.

With conventional x-ray CT devices, the number of image data slices captured in a single investigation is in the range of a few tens of slices. In general, the image is imaged on film using a multiformat camera, and this film is then generally used for observation or reading. However, with multi-beam x-ray CT devices, hundreds of cross-sectional images taken in a single investigation are used in the reproduction of an image, and so imaging these on film with a multiformat camera, and selecting them and observing or reading them is problematic. In light of these considerations, the necessity of constructing a three-dimensional image, and then observing or reading this image is additionally increased.

Thus, multi-beam x-ray CT devices are revolutionary in that they allow the collection of image data having a thin cross-section and cross-section image gap in a shorter period of time than with conventional x-ray CT devices. However, because the number of slices of reconstructed images that are obtained is greatly increased, the load on a network that is transmitting this data is greatly increased, leading to the necessity of high-speed networks. Moreover, picture archival and communication systems (PACS) must also have increased capacity and speed in order to deal with the increase in data. Linked three-dimensional image display devices can receive large quantities of data in a short period of time, and so the necessity has developed for a high-performance system that performs image processing on large quantities of data in a short period of time.

In terms of three-dimensional display methods used with medical images, there are surface rendering techniques whereby the shape of the domain surface is displayed after extracting the domain surface of the object that constitutes the specimen, and volume rendering techniques that treat the specimen as a three-dimensional array of voxels having values corresponding to physical properties.

The surface rendering method creates a three-dimensional image of the object to be displayed by means of the following processes carried out on each of numerous x-ray CT images. 1) extraction of a domain containing an object by threshold value processing that designates an upper and lower limit for CT values held by an object, 2) extraction of the domain of a display object by means of eliminating domains not related to the display object from this domain, 3) extraction of the contour of this domain, 4) production of a solid using the respective contours obtained from multiple slices of the x-ray CT image, and 5) final shadowing and projection processing on the solid, thereby displaying the object to be displayed as a three-dimensional image.

Volume rendering techniques handle voxels possessing opacity and color data corresponding to the physical properties of a specimen as a three-dimensional array, and by carrying out shadowing and projection processing, referred to as ray casting, on this array, the physical properties of a specimen are displayed as a three-dimensional image. Because each voxel possesses color and opacity levels corresponding to the CT values thereof, it is possible to display domains having different CT values as different colors and opacities.

With volume rendering techniques, 1) a three-dimensional voxel array is constructed using x-ray CT image data from multiple slices, 2) the color and opacity are set for a range of CT values possessed by the object of interest, and 3) shadowing and imaging processing known as ray casting are carried out, thereby displaying the object of interest as a three-dimensional image. By setting different colors and opacities for different CT value ranges, it is possible to display domains having different CT values as different colors and opacities.

Although it is necessary to carry out domain extraction for each of the multiple x-ray CT image slices when using the surface rendering technique, a domain extraction operation is not necessary with the volume rendering technique. With the human body, there are many cases where CT values vary continuously in a boundary domain having two anatomical structures, and so the effect of eliminating the domain extraction work is significant. In addition, in comparison to surface rendering techniques, a more natural and smooth shading can be obtained for edges having boundaries that change abruptly.

With volume rendering techniques, three-dimensional voxel arrays constructed using x-ray CT image data are classified based on the object, and the anatomical structural elements of the specimen are classified based on CT values. Consequently, spatial domains having different CT values can be handled as different objects, but spatial domains having the same CT value, for example, are handled as a single object, even with objects that are in physically distinct locations. This is inconvenient for cases in which spatial domains having the same CT values are to be handled as two or more objects.

Thus, with volume rendering techniques, spatial domains having different CT values can be handled as different objects, but spatial domains having the same CT values are handled as a single object, even when the spatial domains having the same CT values are in physically distinct locations. Consequently, as with operation simulations, for example, when a spatial domain having the same physical properties is to be separated and handled as two or more objects, it is necessary to carry out image processing or manipulations in order to separate spatial domains.

FIG. 1 is a block diagram showing a conventional three-dimensional image display device and its network environment. The x-ray CT device 101 collects x-ray CT data from multiple cross-sections of a specimen, reconstructs them, and produces image data for the multiple cross-sections. The PACS server 102 is an image storage and supply system whereby data is collected and reconstructed image data is stored for multiple modalities including the x-ray CT device 101, and whereby data is transported to users as necessary. The three-dimensional image display workstations 121, 122, 123, . . . are three-dimensional image display workstations that retrieve image data collected and stored by the x-ray CT device 101 or PACS server 102 via a network 111, and then use this image data in order to construct three-dimensional images. The network 111 is a high-capacity, high-speed network whereby large quantities of image data are transmitted to three-dimensional image display devices from an x-ray CT device 101 or PACS server 102. The user that constructs the three-dimensional image employs a three-dimensional image display workstation 121, 122 or 123, where image data is obtained from the x-ray CT device 101 or PACS server 102 via the network 111, and this data is then used in constructing the three-dimensional image.

FIG. 2 is a block diagram showing an example of a conventional workstation structure. The central processor 301, memory 302, display processing circuitry 303, display device 304, computer bus 305, data storage device 306, network interface 307 and control device 308 that constitute the workstations all have the same functions as with common personal computers, but a system in which the performance of these constitutive elements is enhanced is commonly used. The high-speed computing device 309, high-capacity memory 310 and high-speed computater bus 311 are commonly used in work-stations in order to process large amounts of information at high speed. The workstations have high image processing capacity relative to common personal computers, and in general are higher in cost.

FIG. 3 is a block diagram showing the function of a conventional three-dimensional image display device. The three-dimensional image display workstation 121 acquires image data via a high speed network 111 from an x-ray CT device 101 or PACS server 102. The data storage device 201 is a magnetic disk device or other such device, which stores the acquired data. The image data selected by the data indicator panel 228 through operation of the control device 211 is designated by a data designation signal 229 read from the data storage device 201, and transferred to the preprocessor 202. After correction of the slice gap and correction of the frame inclination angle performed at the preprocessor 202, the data is stored as voxel data in a three-dimensional voxel storage device 203.

The object setting part 221 is a subsystem for setting the parameters to be used in constructing a three-dimensional image from both the space domain and CT value ranges. Numerous subsystems 221-1, 221-2, 221-3, . . . are provided for establishing multiple objects. The object space domain setting subsystems 222-1, 222-2 . . . , set the parameters of the various object space domains. The object parameter setting subsystems 223-1, 223-2, . . . set the opacity and color as functions of the object CT values. The object parameters 224-1, 224-2, . . . are stored as these set values.

Image processing is carried out using object parameters 225 established by the subsystem 221 for the voxel data of the three-dimensional voxel storage device 203, and the processing results are stored in three-dimensional voxel 204. The three-dimensional voxel 204 retain density, gradient and color values in the space location corresponding to the voxel data in the three-dimensional voxel storage device 203.

The ray casting operation part 205 involves ray casting using projection parameters 227 established by the subsystem 226 which sets the projection processing for voxel data that is stored in the three-dimensional voxel 204 having density, gradient and color values. By this means, the volume-rendered image data is constructed.

The volume-rendered image data produced by the ray casting process at the ray casting operation part 205 is subjected to post-processing involving affine transformation (data compression) at a post-processor 206. Subsequently, the image is displayed on the CRT display or liquid crystal display of the image display device 207.

The control device 211 is used for data designation, object parameter setting, and projection process parameter setting, and is operated by a keyboard or mouse.

Because it is necessary to transport a large quantity of data from the x-ray CT 101 or PACS server 102 in FIG. 3 to the three-dimensional image display workstations 121, traffic on the network 111 is high. Because it is necessary for the transport time to be short in order that the users can function efficiently, a high-speed, high-capacity network is generally used for the network 111. In addition, because the data storage device 201, and the preprocessor 202, three-dimensional voxel storage device 203, three-dimensional voxel 204, ray casting operation part 205 and post-processor 206 in the three-dimensional image display workstation 121 are parts that carry out image processing using large amounts of data, it is necessary for them to have rapid responses in order to prevent stress on the part of the user. Consequently, high-speed image processing is required in these parts, and a high-speed workstation is commonly used to this end for the three-dimensional image display device.

Because it is easy to grasp the solid structure of a specimen more readily from a three-dimensional image than from a two-dimensional image, three-dimensional image display devices are widely used. However, skill is necessary in operating the device so that a diagnostically useful, three-dimensional image is obtained via surface rendering techniques as well as the volume rendering techniques. In addition, because a large quantity of data is used in order to produce a three-dimensional image, a high-speed network is required in order to rapidly transport large quantities of data, and a high-capacity, high-speed data processor is required that can process large quantities of data in a short period of time. Consequently, it is often the case that a specialist will produce three-dimensional images. However, when reporting to the requesting department, he/she only sends a printed copy or simply a written diagnosis. Currently, there are few situations where a three-dimensional imaging device is used at the requesting department in order to produce a three-dimensional image for diagnostic use.

SUMMARY OF THE INVENTION

The present invention was developed in order to solve the above problems, and to this end, offers a three-dimensional image display device in a network environment wherein a three-dimensional image processing server is situated in the vicinity of an x-ray CT device or PACS server network, imaging is carried out whereby a three-dimensional image is produced from the x-ray CT image data by the three-dimensional image processing server, parameters required for producing a three-dimensional image at the three-dimensional image processing server are designated in the respective personal computers that are linked to the network, and the three-dimensional images constructed at the three-dimensional image processing server are displayed on the respective personal computers. The central three-dimensional image processing server performs processing of large amounts of x-ray CT image data in order to construct a three-dimensional image, and each of the personal computers that is linked to the network may be used to designate parameters required for constructing the three-dimensional image by the three-dimensional image processing server, and to display the three-dimensional images produced by the three-dimensional image processing server.

The user that performs three-dimensional image processing of the x-ray CT image data first designates x-ray CT data to be used in constructing the three-dimensional image using the personal computer, and designates parameters such as object space domains and CT value ranges, and projection processing parameters for three-dimensional image display. When this occurs, the image processing server will construct a three-dimensional image, and the results will be sent to the personal computer, which will then display the resulting image.

A single user thus can share a three-dimensional image process with a number of users by designating x-ray CT data to be used in constructing the three-dimensional image from a single personal computer, designating parameters such as object space domains and CT value ranges, and designating projection processing parameters for three-dimensional image display, allowing production of a three-dimensional image by the three-dimensional image processing server, and transmitting the results to multiple personal computers, which then each display the resulting image. For example, it is possible for radiology specialists and the referring physician in the requesting department to simultaneously observe the three-dimensional image that is being constructed. This improves understanding on the part of the referring physician by facilitating mutual understanding between the referring physician and the radiographic specialist. This stands in contrast to cases where the three-dimensional image constructed by a radiographic specialist is sent via film, etc., to the referring physician of the requesting department.

In the past, users performing three-dimensional image processing using x-ray CT image data have employed workstations for three-dimensional image processing connected to an x-ray CT device or PACS server. In this system, the x-ray CT data that is used in order to construct the three-dimensional image is transmitted from the x-ray CT device or PACS server to the three-dimensional image processing workstation, and the three-dimensional image is constructed at this workstation based on the designation of object space domains or CT value range parameters and designation of projection processing parameters for three-dimensional image display, followed by display of the resulting image. For this reason, it is necessary to install costly three-dimensional image processing workstations at each site where a worker is to perform three-dimensional image processing. In addition, it is necessary to lay out a high-speed high-capacity network between locations where each of the users is to perform three-dimensional image processing so that a large volume of x-ray CT data used in order to construct the three-dimensional image can be transferred from the x-ray CT device or PACS server to the workstations for three-dimensional image processing. Network traffic is also increased.

The term "object" used herein is an anatomically-related domain, and is a collection of image elements having CT values in the designated CT value ranges located in the designated space domain.

The term "object parameters" used herein are parameters that define the object, designate the space domain in which the image elements that constitute the object are present, and designate the CT value ranges possessed by the image elements that constitute the object. Opacity and color corresponding to the set CT values are designated in the image elements that constitute the object. Three-dimensional data is constructed by using object parameters to operate on the three-dimensional voxel image element values.

The term "projection processing parameters" refers to the parameters used when an image of a three-dimensional object is constructed by projection.

BRIEF DESCRIPTION OF THE DRAWINGS

The description below refers to the accompanying drawings, in which.

DESCRIPTION OF THE PREFERRED EMBODIMENTS

Figure 1:
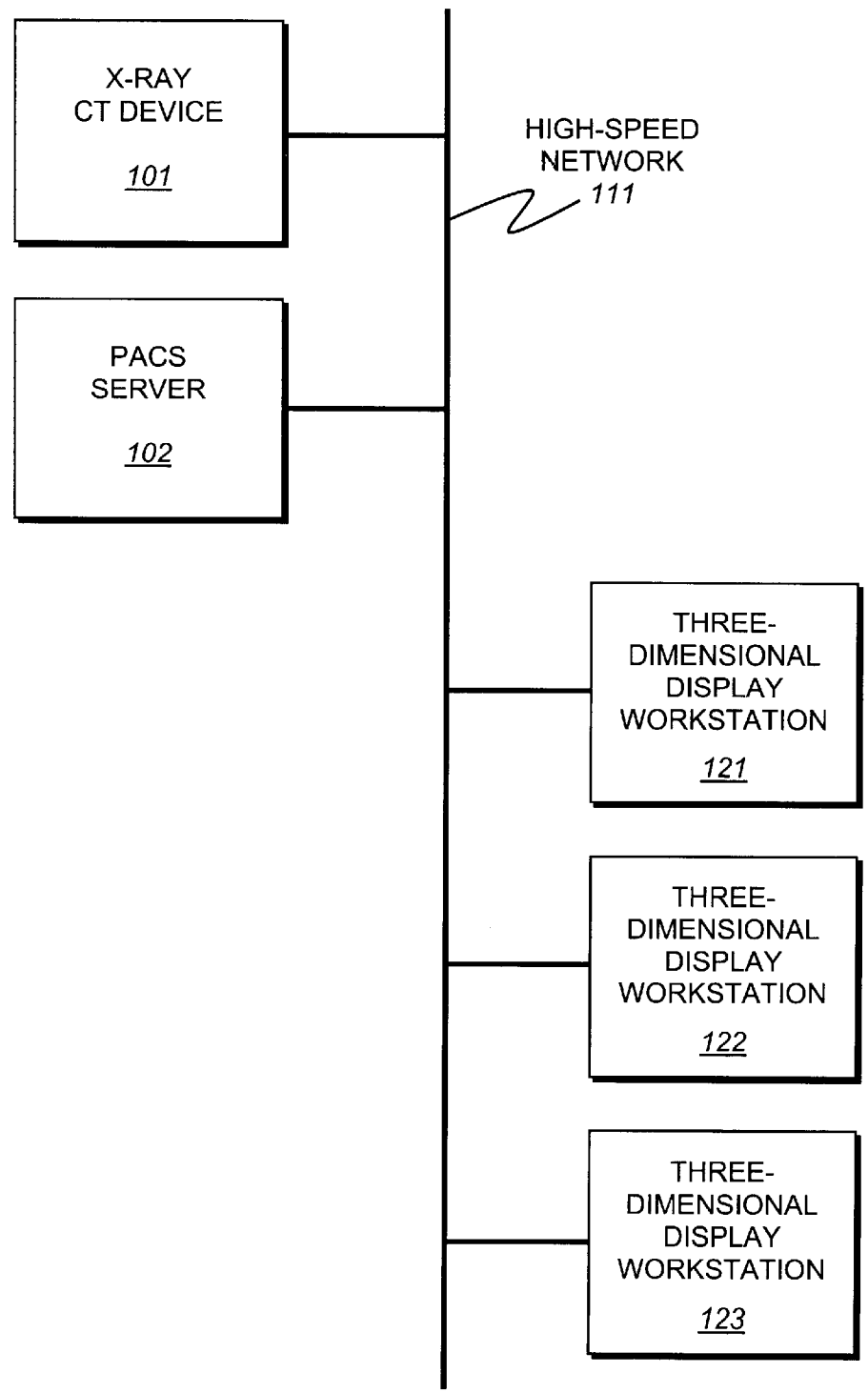
FIG. 1 already described, is a block diagram showing a conventional three-dimensional image display device and its network environment.
Figure 2:
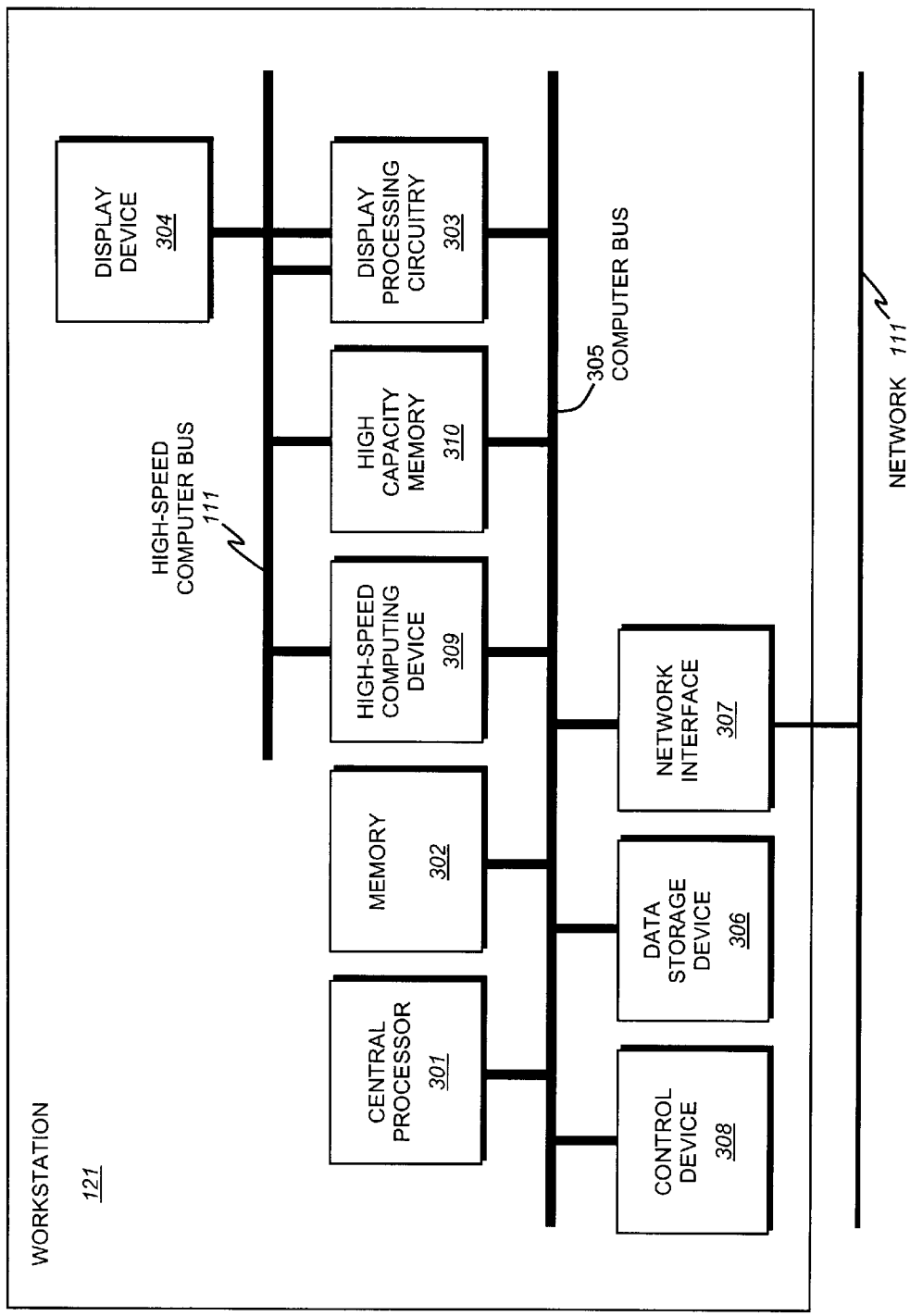
FIG. 2, already described, is a constitutive block diagram of a conventional workstation.
Figure 3:
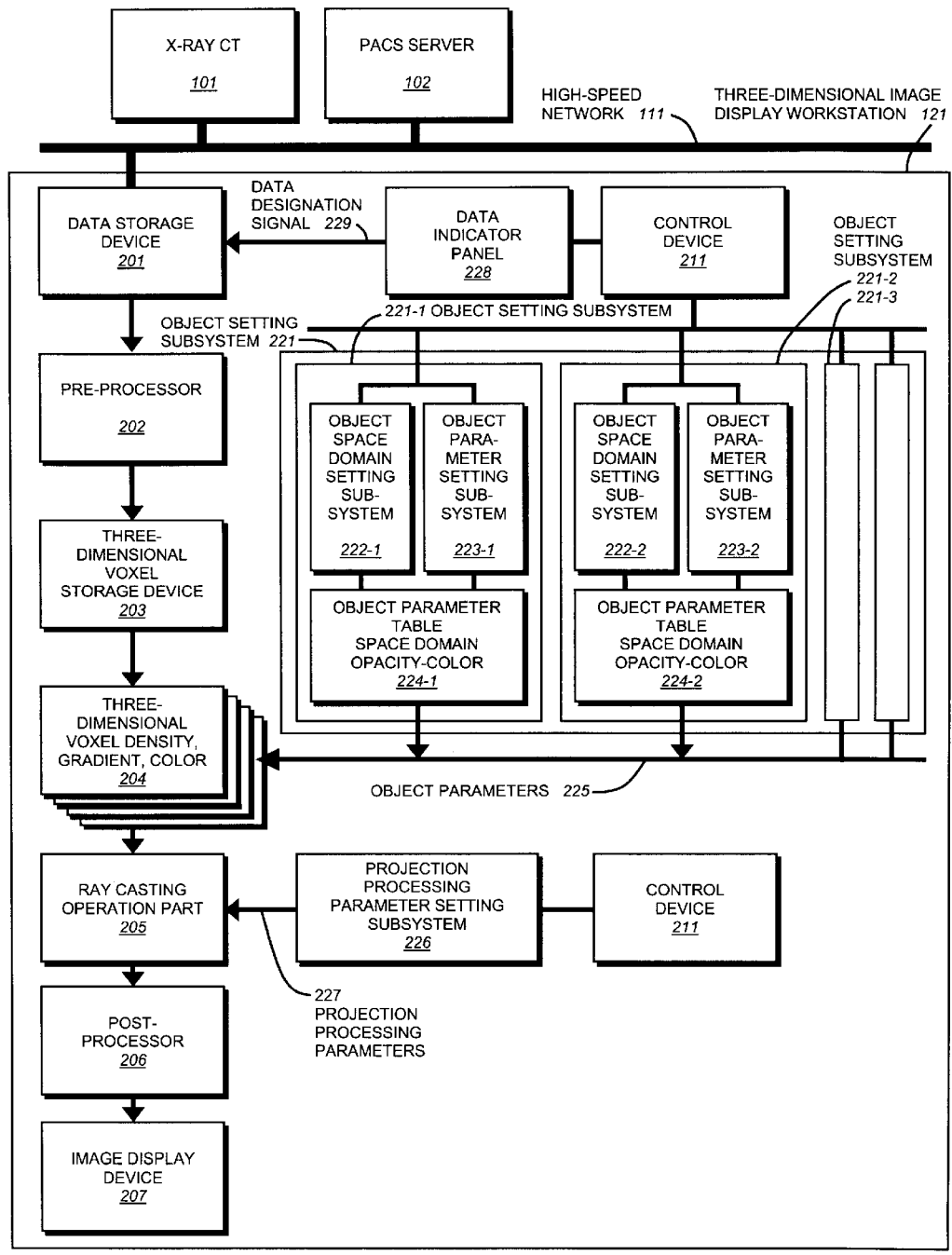
FIG. 3, already described, is a functional block diagram of a conventional three-dimensional image display device.
Figure 4:
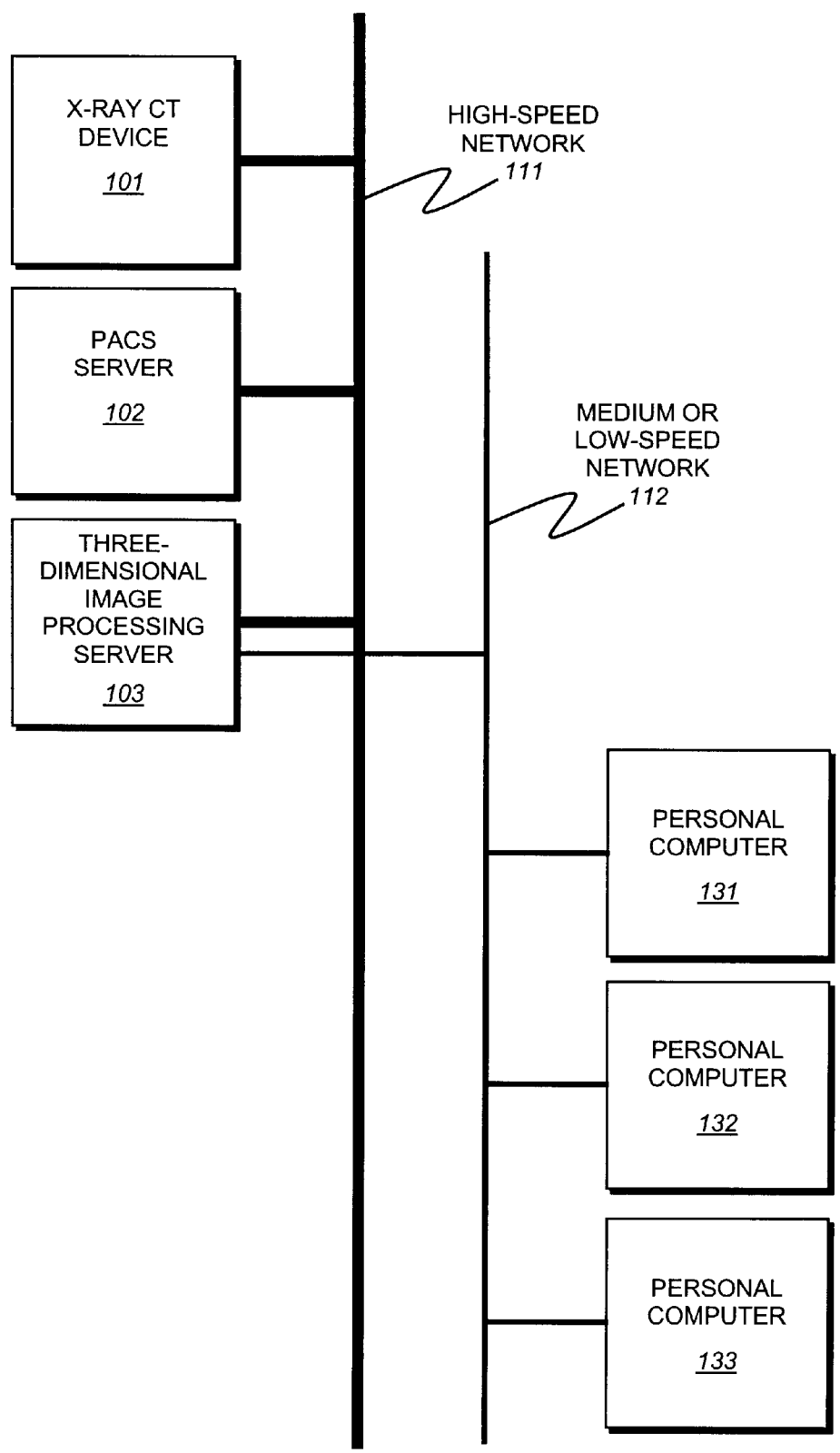
FIG. 4 is a block diagram of a three-dimensional image display system in a network environment pertaining to an embodiment of the present invention.

The three-dimensional image display device in a network environment pertaining to the present invention is described below. FIG. 4 is a block diagram presenting the three-dimensional image display device in a network environment of the present invention and the network environment thereof. The x-ray CT device 101 collects x-ray CT data for multiple cross-sections of a specimen, and reconstructs image data. The PACS server 102 is the server for the image storage and transmission system which combines multiple modalities including the x-ray CT device 101, stores reconstructed image data, and transmits this data as necessary under direction of the users. The three-dimensional image processing server 103 has a server function whereby it acquires and stores image data from the x-ray CT device 101 and PACS server 102, and a three-dimensional image processing function whereby it constructs a three-dimensional image using this data. It also has a function whereby it performs three-dimensional image processing of image data as directed by the personal computers 131, 132, 133, . . . and transmits the constructed three-dimensional images to the personal computers 131, 132, 133, . . .

The personal computers 131, 132, 133, . . . determine image data to be processed by the three-dimensional processing server 103, and also determine the parameters for three-dimensional image processing, while also having a capacity for displaying the constructed and transmitted three-dimensional images. The network 111 is a high-capacity high-speed network whereby large quantities of image data from the x-ray CT device 101 or PACS server 102 are sent to the three-dimensional image processing server 103. The network 112 is a network used for sending instructions from the personal computers 131, 132, 133, . . . to the three-dimensional image processing server 103, and for sending three-dimensional images to be sent from the three-dimensional image processing server 103 to the personal computers 131, 132, 133, . . .

Figure 5:
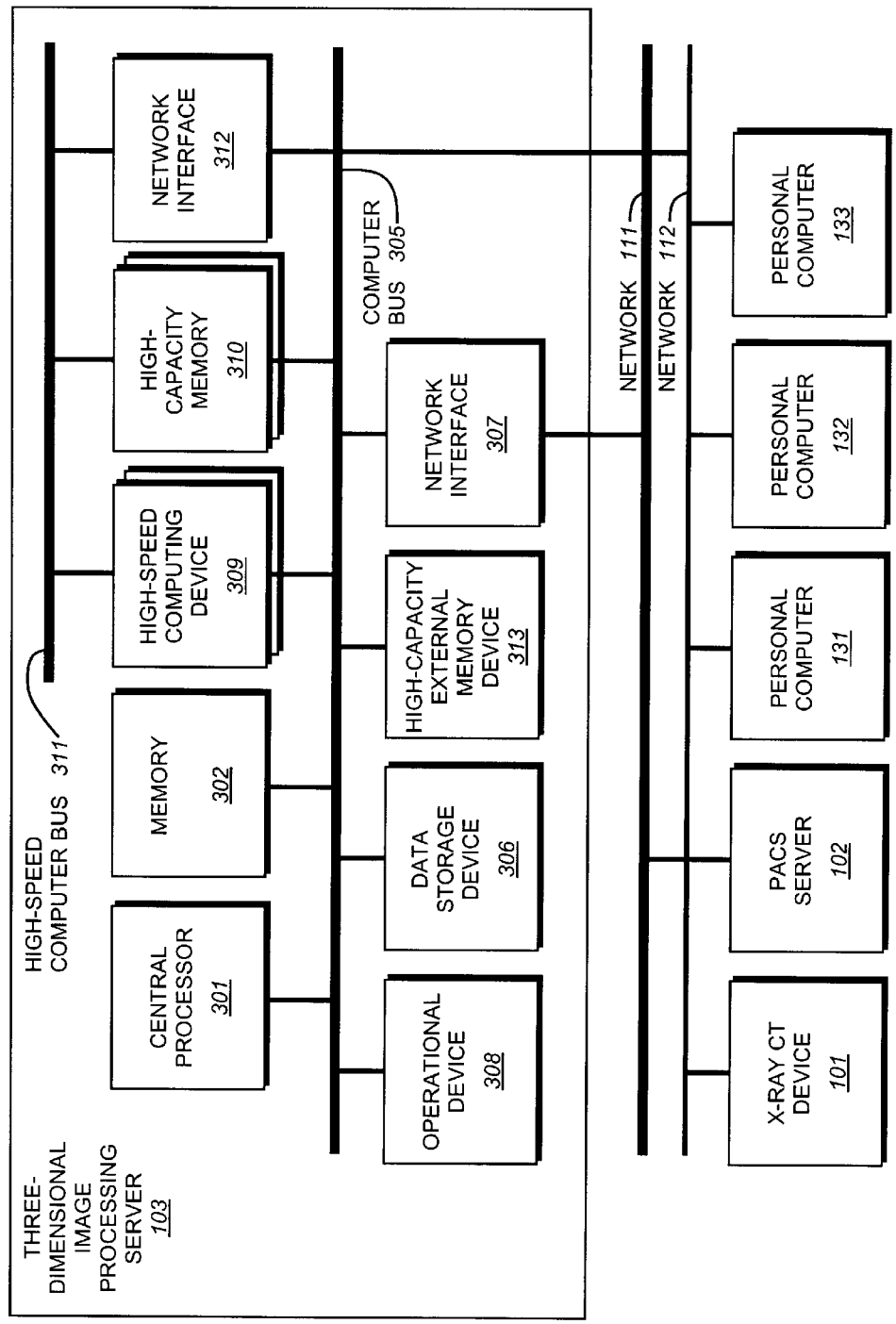
FIG. 5 is a constitutive block diagram of a three-dimensional image processing server pertaining to said embodiment of the present invention.

FIG. 5 is a block diagram showing an embodiment of the three-dimensional image processing server structure. The central processor 301, memory 302, computer bus 305, data storage device 306 and network interface 307 all have the same functions as in common personal computers, but a system in which the performance of these constitutive elements is enhanced is commonly used. The high-speed computing device 309, high-capacity memory 310 and high-speed computer bus 311 are all used for high-speed processing of large quantities of data. The network interface 312 is a network interface that is used for sending instructions from the personal computers 131, 132, 133, . . . to the three-dimensional image processing server 103 via the network 112, and for sending three-dimensional images from the three-dimensional image processing server 103 to the personal computers 131, 132, 133, . . . .

Figure 6:
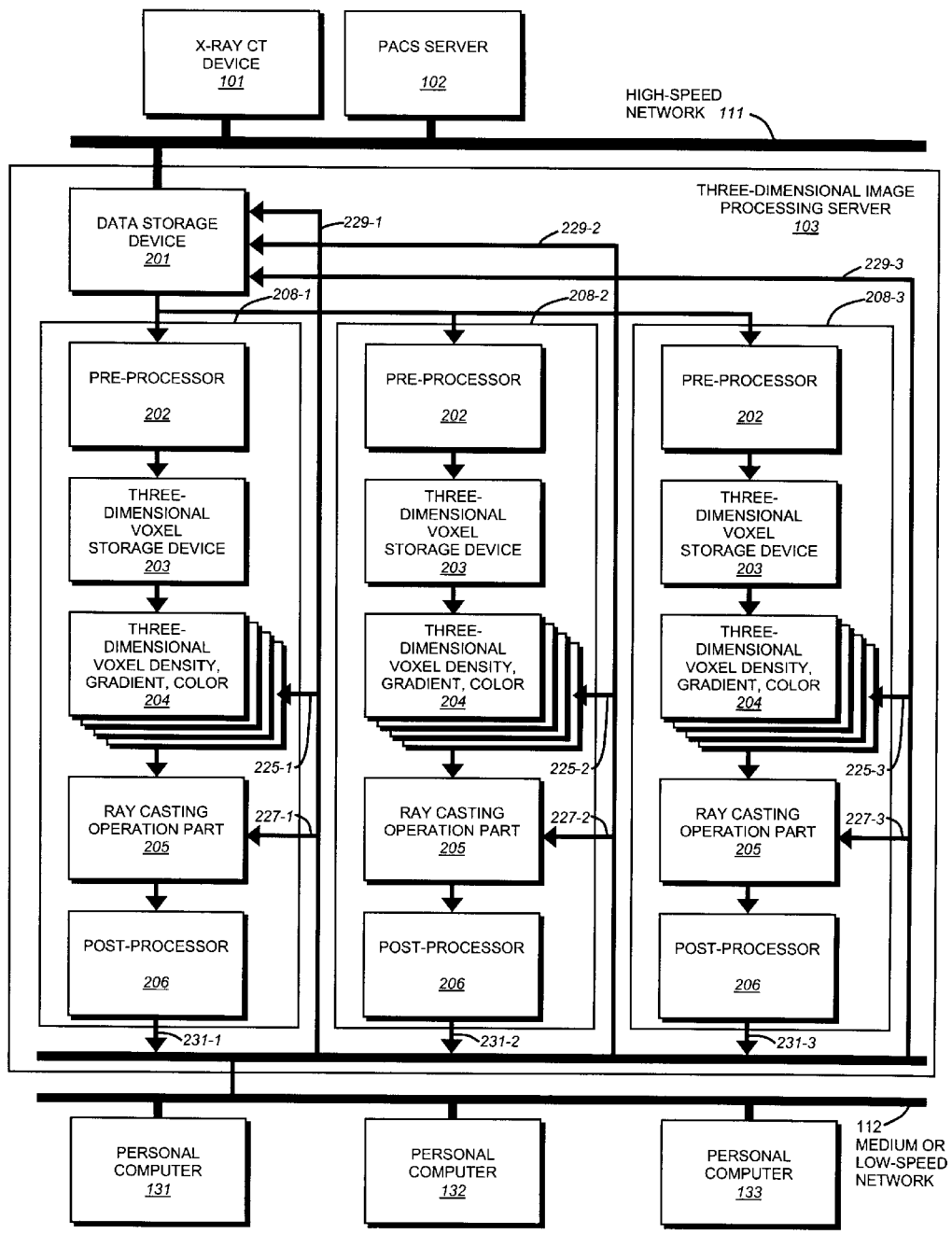
FIG. 6 is a functional block diagram of a three-dimensional image processing server pertaining to said embodiment of the invention.

FIG. 6 is a block diagram showing the functions of the three-dimensional image processing server. The three-dimensional image processing server 103 acquires image data from the x-ray CT device 101 or PACS server 102 via the high speed network 111. The three-dimensional image processing server 103 is connected with the personal computers 131, 132, 133, . . . via the medium or low speed network 112.

The data storage device 201 uses a magnetic disk or other device to store data acquired via the network 111. The data selected by the personal computers 131, 132, 133, . . . is read from the data storage device 201 in accordance with a data designation signal 229,-1, 229-2, 229-3, . . . and is transmitted to the pre-processor 202. After correcting the frame inclination angle and slice gap at the pre-processor 202, the data is accumulated as voxel data in a three-dimensional voxel data storage device 203. The image processing blocks 208-1, 208-2, 208-3, schematically represent that image processing is carried out in parallel in the three-dimensional image processing server. In FIG. 6, the image processing blocks are indicated as three units, but the number of units is not restricted to three.

The voxel data in the three dimensional voxel data storage device 203 is used in order to perform image processing based on the object parameters 225-1, 225-2, 225-3, . . . designated at the personal computers 131, 132, 133 . . . . The processing results are then incorporated into a three-dimensional voxel 204. This three-dimensional voxel 204 retains values for density, gradient and color at spatial locations corresponding to the three-dimensional voxel storage device 203.

Ray casting processing is then carried out at the ray casting operation part 205 using the projection parameters 221 designated by the personal computers 131, 132, 133, . . . with respect to the voxel data retained in the three-dimensional voxel 204 that contain density, gradient and color values. Volume-rendered image data is thus constructed.

The volume-rendered image data constructed by ray casting at the ray casting operation part 205 is then subjected to post-processing such as affine transformation, including data compression, at the post-processor 206, and is then sent via the network 112 to the personal computers 131, 132, 133, . . . .

The three-dimensional image processing server 103 has a powerful high-speed computer device, a high-capacity memory and high-speed computer bus, and thus can carry out parallel three-dimensional image processing operations in close to real time.

Figure 7:
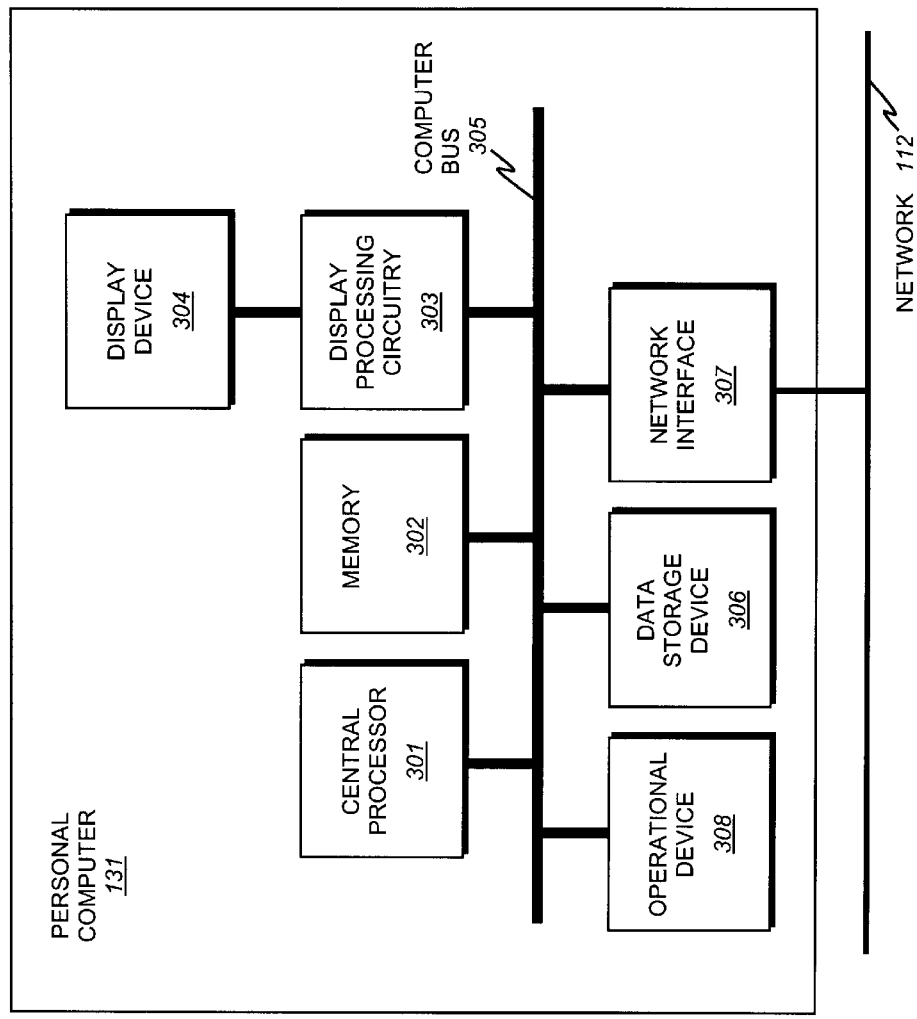
FIG. 7 is a constitutive block diagram of a personal computer.

FIG. 7 is a block diagram showing an example of the structure of the personal computers 131, 132, 133, . . . . The system is constituted by a central processor 301, memory 302, display processing circuitry 303, display device 304, computer bus 305, data storage device 306 and network interface 307. The network interface 307 is a network interface that is used for sending instructions from the personal computers 131, 132, 133, . . . to the three-dimensional image processing server 103 via the network 112, and for sending three-dimensional images from the three-dimensional image processing server 103 to the personal computers 131, 132, 133, . . . .

Figure 8:
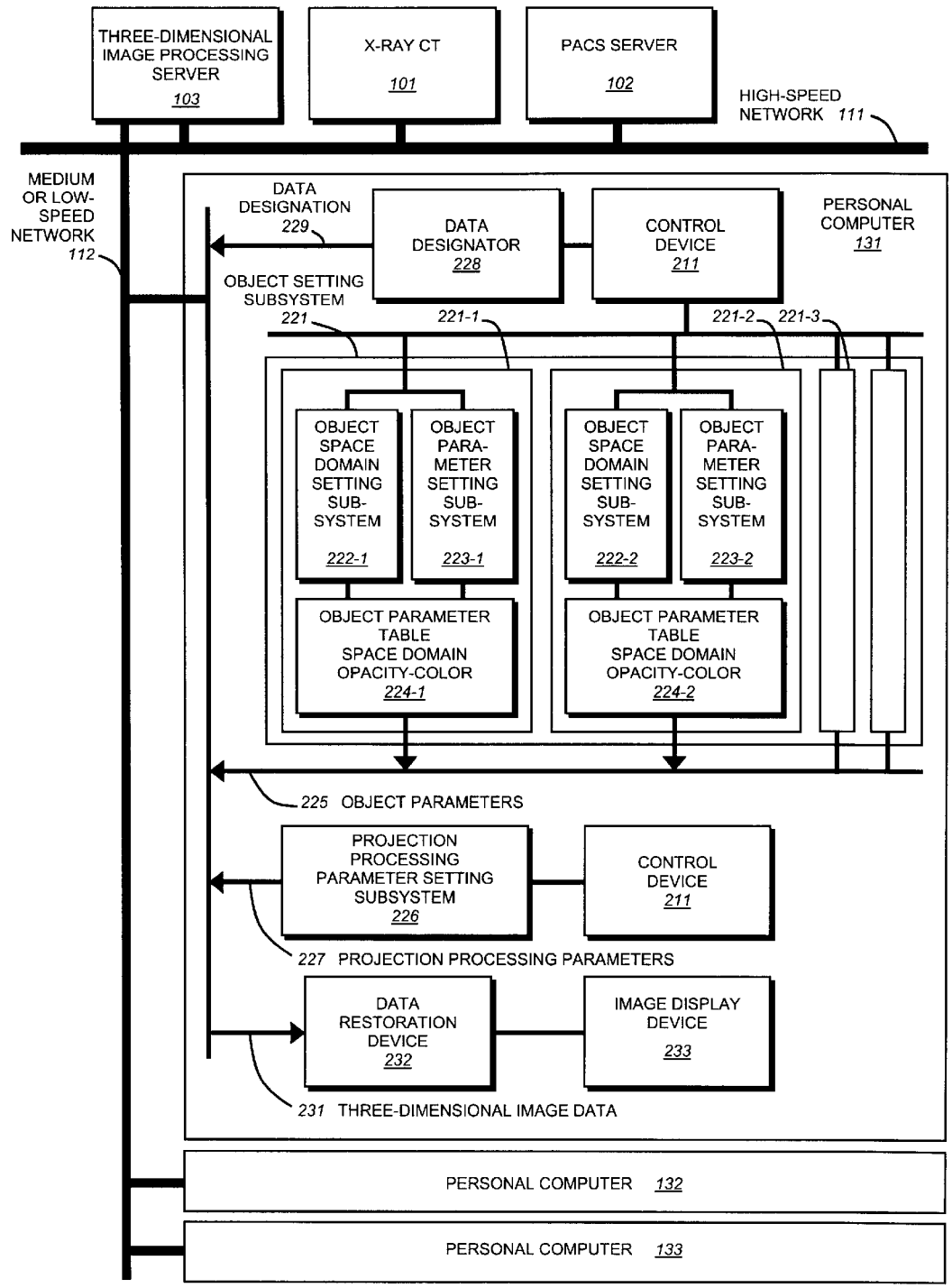
FIG. 8 is a functional block diagram of an operational personal computer pertaining to said embodiment of the present invention.

FIG. 8 is a block diagram showing the function of the personal computers. The personal computers 131, 132, 133, . . . are connected with the three-dimensional image processing server 103 via the network 112.

The data designator 228 designates data to be used in three-dimensional image production at the three-dimensional image processing server 103 by means of operating a control device 211. The information related to the selected data is sent to the three-dimensional image processing server 103 via the network 112 as a data designation control signal 229.

Subsystem 221 sets the parameters for constructing a three-dimensional image from both the space domain and CT value ranges. In order to set multiple objects, multiple subsystems 221-1, 221-2, 221-3, are provided. The object space domain subsystems 222-1, 222-2, . . . set the parameters of the various object space domains. The subsystems 223-1, 223-2, . . . set the opacity and color as functions of the object CT values. The object parameter tables 224-1, 224-2, . . . store these set values. The set parameters are transmitted as object parameters 227 to the three-dimensional image processing server 103 via the network 112.

The projection processing parameter setting subsystem 226 sets the projection processing parameters by which ray casting processing is to be carried out. The projection processing parameters 227 that have been set are transmitted to the three-dimensional image processing server 103 via the network 112.

The volume-rendered image data constructed by means of ray casting at the ray casting operation part 205 of the three-dimensional image processing server 103 is subjected to post-processing such as affine transformation at the post-processor 206, and is transmitted to the personal computers 131, 132, 133, . . . via the network 112. The image data 231 is subjected to data recovery processing in data restoration device 232, and is then displayed on the CRT display or liquid crystal display of the image display device 233.

The control device 211, for example, is used to carry out data designation, object parameter setting, and projection process parameter setting by means of a keyboard and mouse.

In the past, three-dimensional image processing has been carried out with a single three-dimensional image processing workstation, but in the present invention, three-dimensional image processing is achieved by sharing a three-dimensional image processing server among personal computers connected via a network. In the past, a single three-dimensional image processing workstation was used for each worker when three-dimensional image processing was to be carried out by multiple users, but with the present invention, processing is carried out using a single central three-dimensional image processing server and a personal computer for each user.

The multiple users can carry out shared three-dimensional image processing by sharing a single, central, three-dimensional image processing server among the individual personal computers of each user. Thus, whereas a single three-dimensional image processing workstation was used for each user in the past when multiple users were each carrying out three-dimensional image processing, now with the present invention, it is possible to carry out processing by sharing a single central three-dimensional image processing server among the individual single personal computers of each user. This system provides the advantages discussed below.

The area over which a high-speed network must be laid out in a hospital or other setting can be decreased. Specifically, when establishing a single three-dimensional image processing workstation for each of the users in a situation where there are multiple users, it was necessary to lay out a high-speed network between the X-ray CT device or PACS server and the numerous three-dimensional image processing workstations. However, with the present invention that employs a single central three-dimensional image processing server and personal computers for each of the users, it is not necessary to provide a high-speed network between the x-ray CT device or PACS server and the three-dimensional image processing server. The network running between the three-dimensional image processing server and the multiple personal computers need only be a medium or low-speed network.

Traffic on the high-speed network can be reduced. Specifically, when multiple servers used the same image data, it was necessary for each of the image data sets to be transmitted to the respective three-dimensional image processing workstations when individual processing workstations were used by each of multiple users. With the present invention, however, image data need only be sent to the three-dimensional image processing server, and thus the network traffic can be greatly reduced.

A medium or low-speed network to the multiple personal computers can be employed. Thus, the network need not be dedicated to images, and can be shared with systems such as other hospital information systems. In other words, although it is necessary to provide a high-speed network between the x-ray CT device or PACS server and the multiple three-dimensional image processing servers, only a low-speed network need be provided between the three-dimensional image processing server and multiple personal computers.

Multiple users can share the same three-dimensional image processing process. A single user uses a personal computer to designate x-ray CT data to be used for three-dimensional image production, to designate parameters such as object space domain and CT value ranges, and to designate projection processing parameters for three-dimensional image display, and the results of three-dimensional image production are sent by the three-dimensional image processing server to multiple personal computers. These respective personal computers display the resulting images, and thus multiple users can share the same three-dimensional image processing process. For example, it is possible for a radiographic specialist and the referring physician of the requesting department to simultaneously observe the three-dimensional image during its production.

Equipment expenditures and equipment area can be reduced. Equipment expenditures for a single three-dimensional image processing server and multiple personal computers are less than for multiple three-dimensional image processing workstations. In addition, personal computers require less surface area than workstations.

Figure 9:
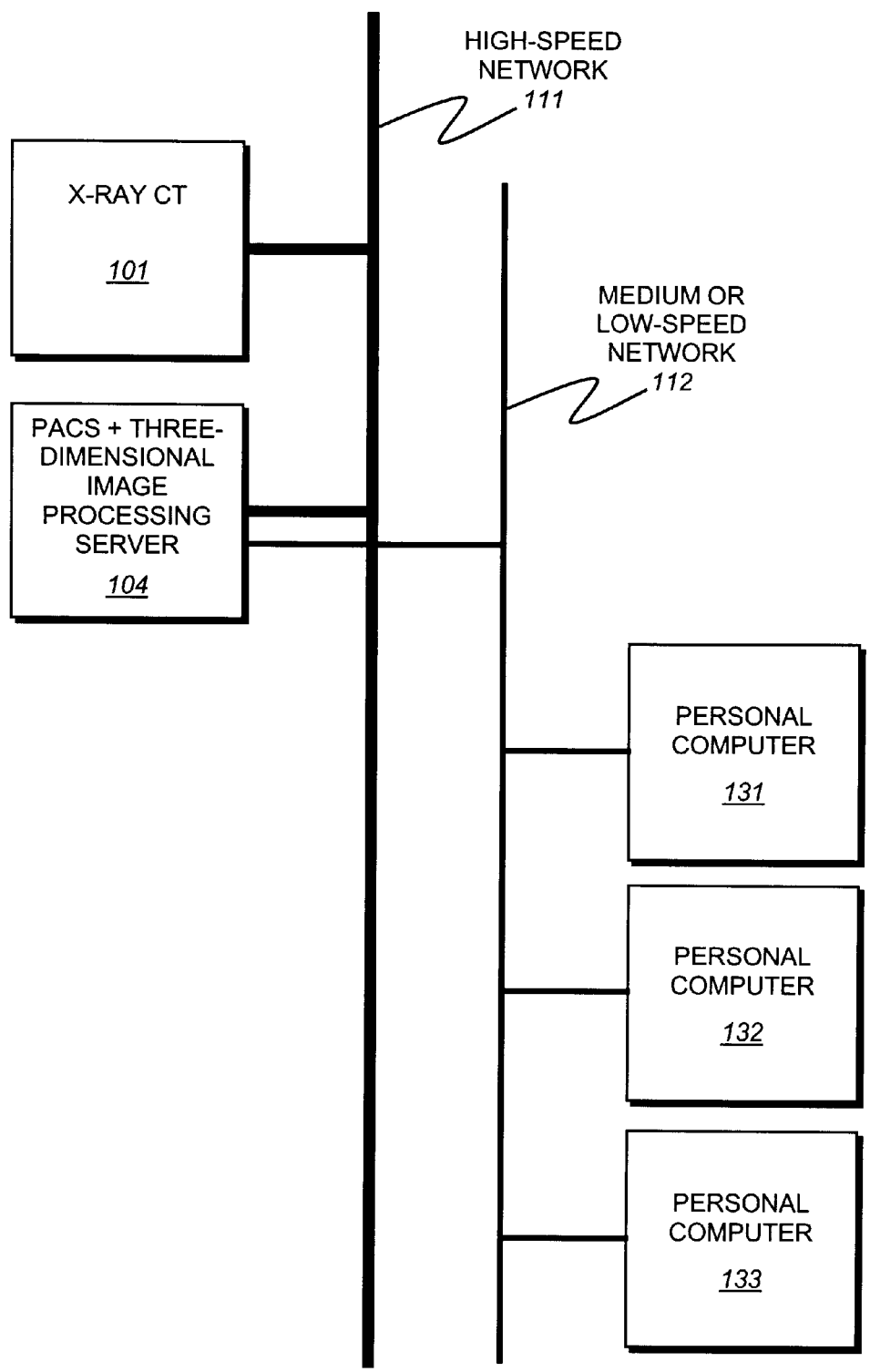
FIG. 9 is a block diagram of a three-dimensional image display system in a network environment pertaining to an another embodiment of the present invention.

FIG. 9 is a block diagram that presents another example of the three-dimensional image display device in a network environment pertaining to the present invention, and the network environment thereof. In this working example, the PACS server 102 and three-dimensional image processing server 103 in FIG. 4 are integrated to produce a PACS server plus three-dimensional image processing server 104. The x-ray CT device 101 acquires x-ray CT data from a number of cross-sections of a specimen, and reconstructs the image data. The PACS plus three-dimensional image processing server 104 stores image data collected from a number of modalities including the x-ray CT device 101, and has a three-dimensional image processing function that constructs three-dimensional images using this data, and an image storage and transfer system server that transmits information for the users as necessary. The server has functionality whereby it performs three-dimensional image processing of designated image data according to instructions from the personal computers 131, 132, 133, . . . , and sends the constructed three-dimensional images to the personal computers 131, 132, 133, . . . . The personal computers 131, 132, 133, . . . are used in order to designate the three-dimensional image processing parameters and the image data that is to be processed by the PACS plus three-dimensional image processing server 104, and have functions whereby they display the three-dimensional images that have been constructed and transmitted. The network 111 is a high-capacity high-speed network whereby large amounts of image data are transmitted from the x-ray CT device 101 or PACS server 102 to the three-dimensional image processing server 103. The network 112 is a network used for transferring three-dimensional images sent from the three-dimensional image processing server 103 to the personal computers 131, 132, 133, . . . and for transferring instructions from the personal computers 131, 132, 133, . . . to the three-dimensional image processing server 103.

Figure 10:
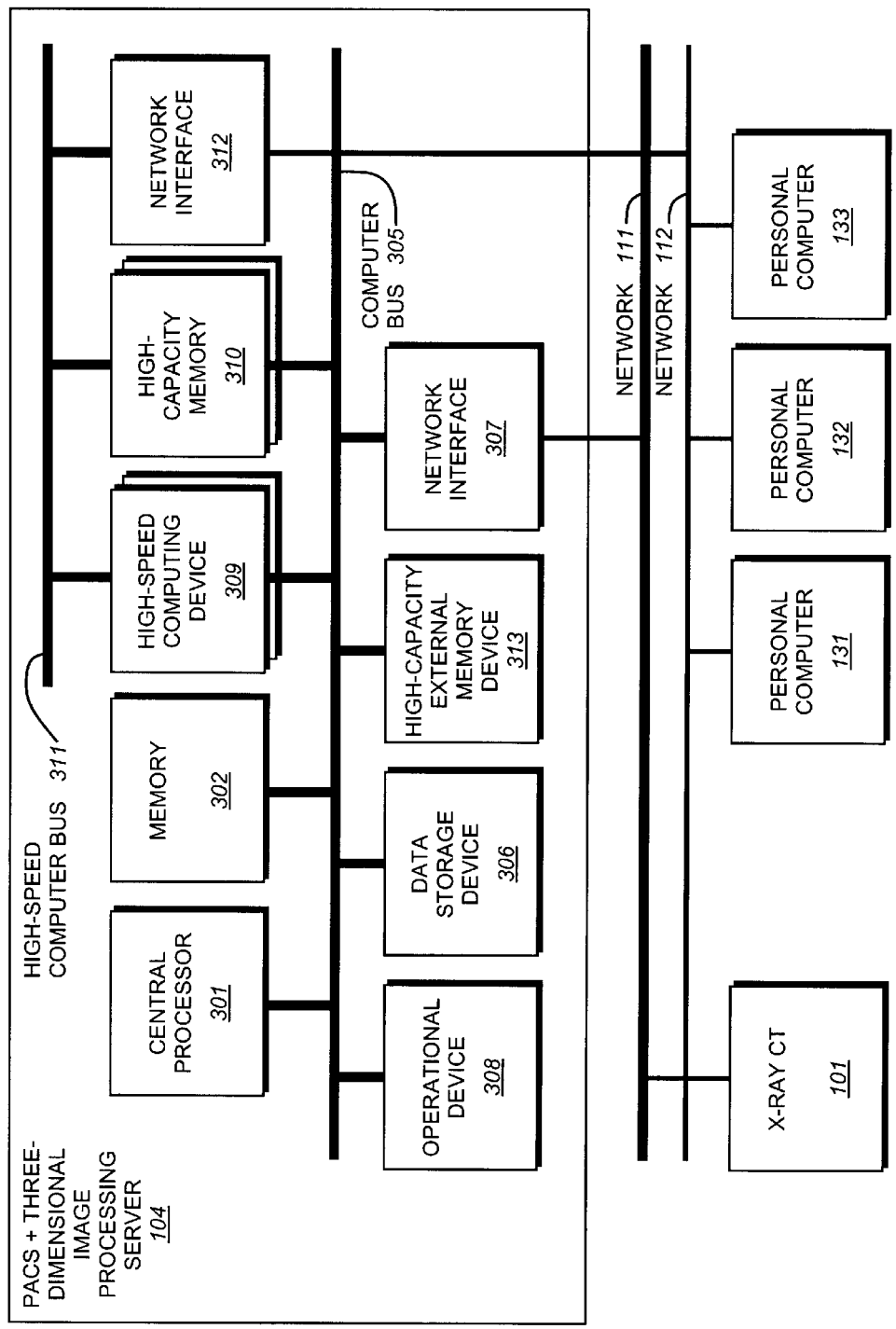
FIG. 10 is a constitutive block diagram of a three-dimensional image processing server pertaining to said another embodiment.

FIG. 10 is a block diagram showing an example of the structure of the PACS plus three-dimensional image processing server. The central processor 301, memory 302, computer bus 305, data storage device 306 and network interface 307 that constitute the workstation all have the same functions as in common personal computers, but a system in which the performance of these constitutive elements is enhanced is commonly used. The high-speed computing device 309, high-capacity memory 310 and high-speed computator bus 311 are commonly used in workstations in order to process large amounts of information at high speed. The network interface 312 is a network interface that is used for sending instructions from the personal computers 131, 132, 133, . . . to the three-dimensional image processing server 103 via the network 112, and for sending three-dimensional images from the three-dimensional image processing server 103 to the personal computers 131, 132, 133, . . . . The structure presented in FIG. 10 is nearly identical to the structure of FIG. 5, but because the PACS server functionality is built in, a high-capacity external memory device 313 is linked.

Figure 11:
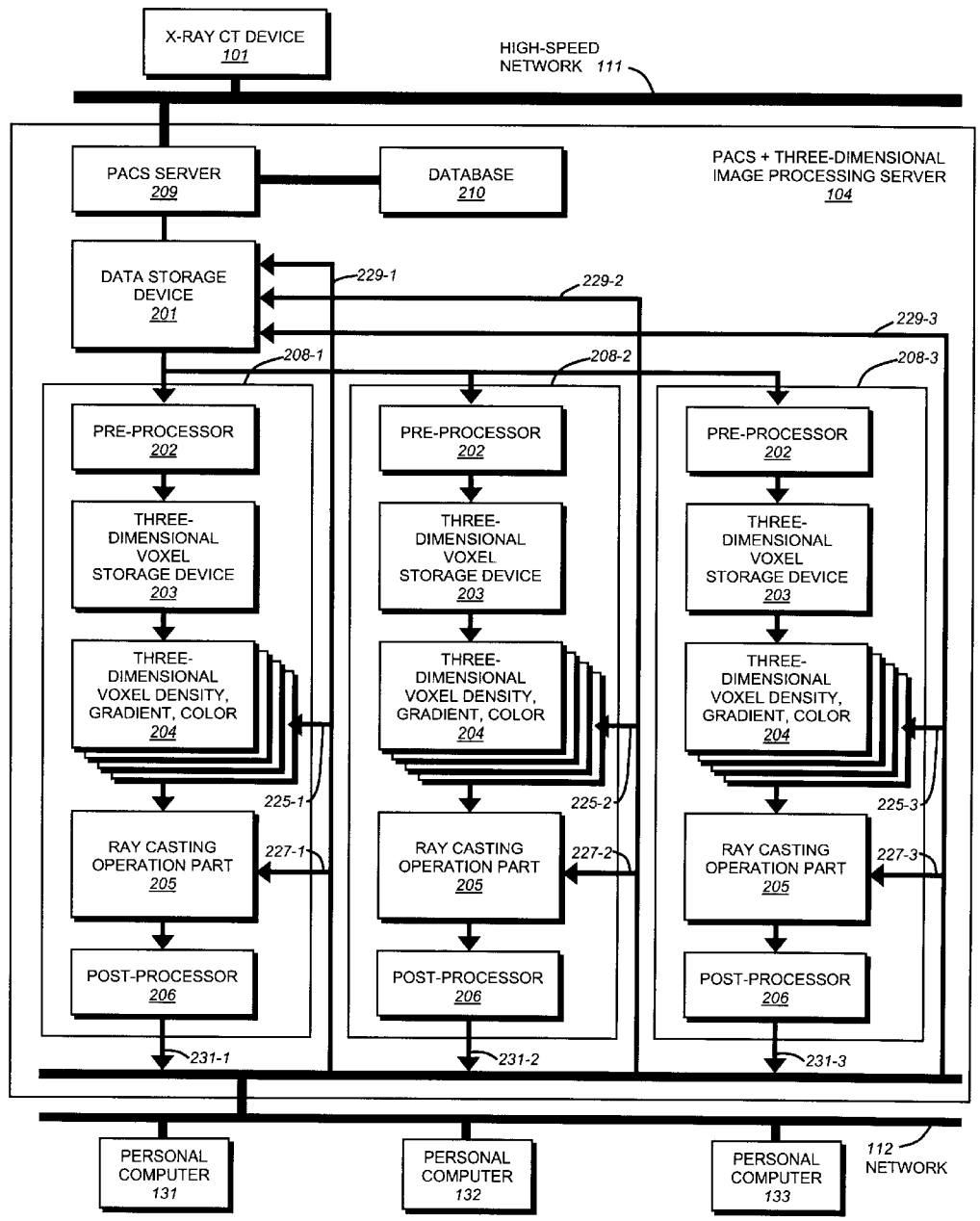
FIG. 11 is a functional block diagram of a three-dimensional image processing server pertaining to said another embodiment of the present invention.

FIG. 11 is a block diagram showing the functionality of the PACS plus three-dimensional image processing server 104. The PACS plus three-dimensional image processing server 104 acquires image data from the x-ray CT device 101 or PACS server 102 via the high speed network 111. The PACS plus three-dimensional image processing server 104 is connected to the personal computers 131, 13 , 133, . . . via the medium or low speed network 112.

The PACS server 209 is constituted by a magnetic disk device and high-capacity external memory device, is connected to modalities such as the x-ray CT device 101 via the network 111, and stores data acquired through modalities such as the x-ray CT device 101. The database is used for managing image data that is stored by the PACS server.

The PACS server 209 and data storage device 201 are connected via a high-speed computer bus. The data that is selected at the personal computers 131, 132, 133, . . . is transmitted from the PACS server 209 to the data storage device 201, is read from the data storage device 201 in accordance with a data designation signal 229, and is transmitted to a preprocessor 202. The subsequent processing flow is the same as in FIG. 6.

The PACS server 209 and data storage device 201 can be connected with a high-speed computer bus, and thus image data used in order to construct three-dimensional images can be acquired in a short period of time.

In the above embodiments, examples were presented that involved an x-ray CT device and x-ray CT image data obtained therefrom. However, exactly the same system can be used for MR devices, devices used for nuclear medicine, ultrasound devices and other medical imaging devices, and the image data obtained therefrom. The system can also function similarly when these medical imaging devices and the image data obtained therefrom are used simultaneously.

The present invention offers a three-dimensional image display device in a network environment, which is equipped with a three-dimensional image processing device having a means for acquiring image data used in three-dimensional image production based on instructions from control computers, a means for preprocessing the image data and incorporating it into three-dimensional voxels, a means for using the object parameters designating colors, opacities and space domains of the multiple objects that constitute a specimen to operate on the three-dimensional voxel element values, thus producing a single three-dimensional data construct, and a means for using the projection processing parameters to operate on the three-dimensional data to construct a three-dimensional image, and which is equipped with multiple control computers having means for designating image data to be used in three-dimensional image processing, means for setting object parameters that designate color, opacity and space domain of the multiple objects that constitute a specimen, means for setting the projection processing parameters that generate the three-dimensional image from the three-dimensional data, means for relaying these instructions to the three-dimensional image processing device and means for displaying the three-dimensional images constructed by the three-dimensional image processing device, and which is equipped with a means for connecting the three-dimensional image processing system and the multiple personal computers via a network.

By also providing the three-dimensional image processing device with an image storage means that functions as an image server for a medical picture archiving and communication system (PACS), and integrating this means therein, the function of image data storage and the function of three-dimensional image production will be closely related in the hospital. As a result, it is possible to decrease network load and increase image data acquisition speed when constructing three-dimensional images.

In the past, three-dimensional image processing was carried out at respective three-dimensional image processing workstations provided for each worker, and thus it was necessary to send image data used for three-dimensional image processing from the x-ray CT device or PACS server to each workstation via a network. As a result, a significant amount of time was required for transmission. According to the present invention, three-dimensional image processing is carried out on a central three-dimensional image processing server, and only the results of image processing are transmitted to the controlling personal computers via the network. Consequently, the time required for network transport of image data can be reduced to nearly zero. This method thus has great merit, particularly in cases where multiple users are using the same image data.

A three-dimensional image processing device is constructed in such a manner that acquisition of image data for producing three-dimensional images, production of three-dimensional voxels, production of three-dimensional data and production of three-dimensional images can be carried out in short periods of time. Other than production and transmission of control signals, the control computers only perform display and signal reception of three-dimensional images constructed by the three-dimensional image processing device. Consequently, it is possible to actually achieve interactivity in terms of display of three-dimensional images and operations on the various computers.

Acquisition of image data for constructing three-dimensional images, production of three-dimensional voxels, construction of three-dimensional data, and production of three-dimensional images are all carried out by a three-dimensional image processing device. Other than production and transmission of control signals, the computers only perform display signal reception of three-dimensional images constructed by the three-dimensional image processing device. Consequently, even if a medium or low-speed network is used as the network for connecting the three-dimensional image processing device and the multiple personal computers, it is possible to actually achieve interactivity in terms of display and operations on three-dimensional images with the computers.

Acquisition of image data for constructing three-dimensional images, production of three-dimensional voxels, production of three-dimensional data, and production of three-dimensional images are all carried out by a three-dimensional image processing device. Other than production and transmission of control signals, the computers only perform display and signal reception of three-dimensional images constructed by the three-dimensional image processing device. Consequently, even if medium or low-speed personal computers are used for the controlling computers, it is possible to actually achieve interactivity in terms of display and operations on three-dimensional images using the computers.

Acquisition of image data for constructing three-dimensional images, production of three-dimensional voxels, production of three-dimensional data, and production of three-dimensional images are all carried out by a three-dimensional image processing device. Other than production and transmission of control signals, the control computers only perform display and signal reception of three-dimensional images constructed by the three-dimensional image processing device. By this means, a three-dimensional image display device in a network environment is offered that allows for simultaneous display of three-dimensional images on numerous computers by operating a single control computer.

The three-dimensional image processing device performs compression of image data at the time that three-dimensional images are sent, and the control computers restore image data at the time of receipt of the three-dimensional images. Consequently, even if a medium or low-speed network is used as the network for connecting the three-dimensional image processing device and the multiple control computers, it is possible to actually achieve interactivity in terms of display response and operations on the three-dimensional images using the multiple computers.

We claim:

1. A three-dimensional image processing system for use in a network environment comprising a three-dimensional image processing device including
means for acquiring image data used in three-dimensional image production based on instructions from control computers,
means for subjecting the image data to pre-processing to incorporate it into three-dimensional voxels,
means for operating on the three-dimensional voxel image element values using object parameters that designate the color, opacity and space domain of the multiple objects that constitute the specimen so at to produce a single three-dimensional data construct, and
means for operating on the three-dimensional data construct using projection processing parameters to construct three-dimensional images;

multiple control computers each including
means for designating image data used in three-dimensional image production,
means for designating object parameters that designate the color, opacity and space domain of the multiple objects that constitute the specimen,
means for setting projection processing parameters for constructing three-dimensional images from three-dimensional data,
means for relaying these instructions to the three-dimensional image processing device, and
means for displaying the three-dimensional images produced by the three-dimensional image processing device, and network means for connecting said three-dimensional image processing device and said control computers.

2. The three-dimensional image processing system in a network environment as defined in claim 1, wherein the three-dimensional image processing device includes an image storage means having an image server function for a medical picture archival and communications system (PACS) to produce an integrated structure, so that the image data storage and three-dimensional image processing are closely linked thereby increasing the speed of acquisition of image data for constructing three-dimensional images, and decreasing network load.

3. The three-dimensional image processing system in a network environment as defined in claim 1 or 2, wherein said three-dimensional image processing device is constituted so that processing related to acquisition of image data for constructing three-dimensional images, production of three-dimensional voxels, production of three-dimensional data and production of three-dimensional images are carried out in a minimal period of time whereby other than production and transmission of control signals, the control computers carry out only receipt and display of three-dimensional images constructed by the three-dimensional image processing device, thereby achieving interactivity in terms of display of three-dimensional images and operations on the control computers.

4. The three-dimensional image processing system in a network environment defined in claim 3, wherein said network means comprise a medium or low-speed network able to achieve interactivity in terms of operation and display of three-dimensional images on the control computers.

5. The three-dimensional image processing system in a network environment defined in claim 3, wherein even when said control computers comprise medium or low-speed computers, it is possible to achieve interactivity in terms of operation and display of three-dimensional images on said control computers.

6. The three-dimensional image processing system in a network environment as defined in claim 1 or 2, wherein
said three-dimensional image processing device carries out acquisition of image data for constructing three-dimensional images, production of three-dimensional voxels, production of three-dimensional data, and production of three-dimensional images and,
other than production and transmission of control signals, said control computers carry out only receipt and display of three-dimensional images constructed by the three-dimensional image processing device, whereby said control computers simultaneously display three-dimensional images by operations carried out on only one of said control computers.

7. The three-dimensional image processing system in a network environment as defined in claim 1 or 2, wherein
the three-dimensional image processing device includes means for compressing image data at the time of transmission of the constructed three-dimensional images, and
the control computers carry out restoration of image data upon receipt of the three-dimensional images, whereby even when said network means comprise a medium or low-speed network, it is possible to achieve interactivity in terms of operation and display response with three-dimensional images on the control computers.

* * * * *